United States Patent
Mills et al.

(10) Patent No.: US 7,277,753 B2
(45) Date of Patent: Oct. 2, 2007

(54) DEFIBRILLATOR

(75) Inventors: Desmond Bryan Mills, IXA Medical Products LLP, 54 Bath Road, Cheltenham, Gloucestershire (GB) GL53 7HG; Kevin Herbert, Gloucestershire (GB)

(73) Assignees: Desmond Bryan Mills, Gloucestershire (GB); Stephen Colin Brown, Gloucestershire (GB); Malcolm Bradley Mills, Gloucestershire (GB)

( * ) Notice: Subject to any disclaimer, the term of this patent is extended or adjusted under 35 U.S.C. 154(b) by 284 days.

(21) Appl. No.: 10/490,265

(22) PCT Filed: Sep. 23, 2002

(86) PCT No.: PCT/GB02/04326

§ 371 (c)(1), (2), (4) Date: Mar. 22, 2004

(87) PCT Pub. No.: WO03/024523

PCT Pub. Date: Mar. 27, 2003

(65) Prior Publication Data

US 2004/0249418 A1    Dec. 9, 2004

(30) Foreign Application Priority Data

Sep. 21, 2001    (GB) .................................. 0122746.1

(51) Int. Cl.
A61N 1/39    (2006.01)

(52) U.S. Cl. .......................................................... 607/5

(58) Field of Classification Search .................... 607/4, 607/5

See application file for complete search history.

(56) References Cited

U.S. PATENT DOCUMENTS

| 5,330,504 | A | * | 7/1994 | Somerville et al. ............. 607/5 |
| 5,447,519 | A | * | 9/1995 | Peterson ......................... 607/5 |
| 5,944,742 | A | | 8/1999 | Brewer et al. |
| 6,029,085 | A | | 2/2000 | Olson et al. |
| 6,064,907 | A | * | 5/2000 | Thong et al. ................ 600/519 |
| 6,393,316 | B1 | * | 5/2002 | Gillberg et al. ............. 600/515 |

* cited by examiner

*Primary Examiner*—Scott M. Getzow
(74) *Attorney, Agent, or Firm*—Young & Thompson

(57) ABSTRACT

A defibrillator incorporates an analyser (2) arranged to receive signals from a patient's heart (such as from electrode pads (6) placed on the patient's chest). A charging circuit (4) enables the electrodes (6) to deliver a charge from the charging circuit to the patient. The analyser is arranged to compare one or more heart rhythm sequences from the patient with predetermined data relating to a heart rhythm and, depending on a result of an initial part of comparison, the analyser is arranged to activate starting of charging of the charging circuit, whilst comparison continues, in readiness for possible delivery of a shock to the patient.

12 Claims, 3 Drawing Sheets

DEFIBRILLATOR

Figure 1:
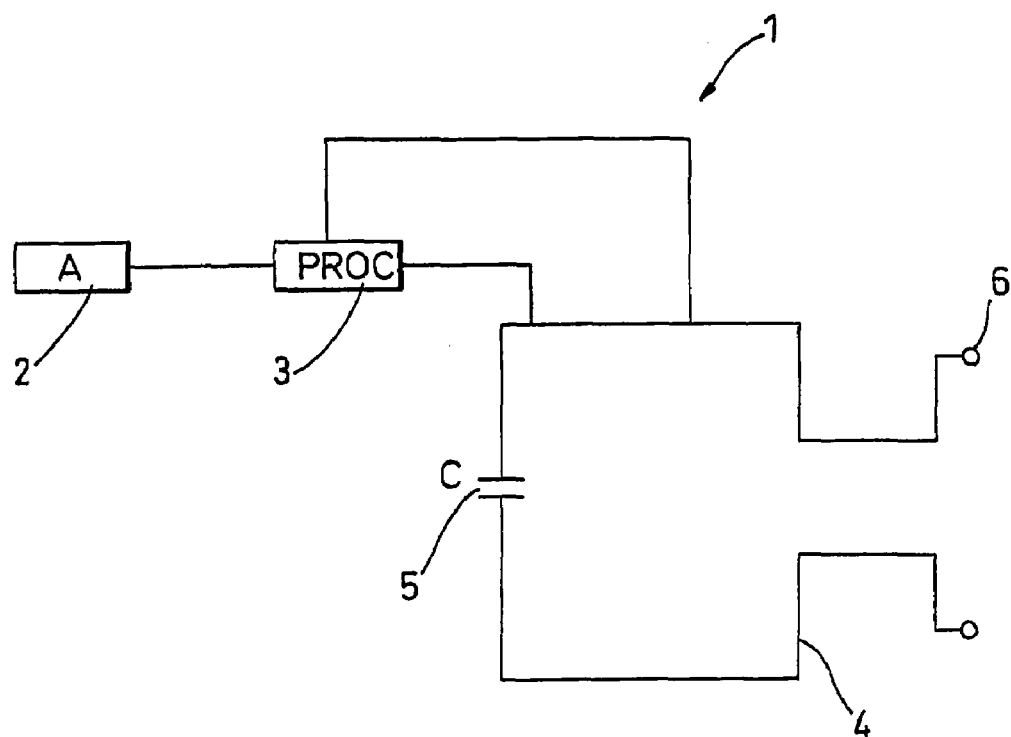

The invention relates to the treatment of heart conditions such as cardiac arrhythmia or heart failure, and more particularly to apparatus and means for the optimum delivery of an electric shock to the heart during such conditions. In particular, the invention is directed to distinguishing between life threatening and non-threatening cardiac rhythms so that delivery of an electric shock only occurs when it is absolutely necessary.

In normal operation, the heart acts as a pump that delivers blood throughout the body. When the heart is pumping blood under normal conditions, the rhythm produced by the heart is termed normal sinus rhythm. In individuals where the heart ceases to function efficiently, the rhythm of the heart is ineffective in delivering blood and produces a primary cardiac arrhythmia, the most common of which is either ventricular fibrillation (VF) or pulseless ventricular tachycardia (VT). The abnormal activity of the heart results from asynchronous depolarisation of cardiac cells in the heart muscle.

It is well known that a high-energy shock, applied to the chest cavity can convert cardiac arrhythmias such as ventricular fibrillation, to normal sinus rhythm. This is known as defibrillation. If sufficient electrical energy is delivered to the heart, the cardiac cells briefly arrest and synchronous or normal depolarisation of the heart muscle may once again resume.

Electrical energy is usually applied by a defibrillator, such as an automated external defibrillator (AED), through a set of pads or paddles applied to the chest.

The survival rate of a patient after the onset of ventricular fibrillation decreases by approximately ten per cent per minute if there is no administration of a high-energy shock to convert the heart rhythm back to a normal sinus rhythm. Consequently, if there is a delay of more than a few minutes, a patient's chance of survival is greatly reduced.

The administration of a defibrillation shock to a patient can be dangerous if the patient's heart is not in fact undergoing ventricular fibrillation. If a normally operating heart is given a high-energy shock by mistake, there is the risk that the normal sinus rhythm of the heart will be disrupted, which can lead to ventricular fibrillation, which could in turn result in heart failure. Further, there may be dangers for the operator if the defibrillator is damaged in any way, because when the defibrillator is accumulating a charge there is the risk that this charge may be discharged through the operator.

When the heart undergoes ventricular fibrillation, the amplitude and waveform of the heart rhythm pattern deteriorates rapidly. When abnormal operation is detected, it is important to apply a shock to the heart as soon as possible. A shockable heart rhythm is one having a rate of greater than 180 beats per minute and a QRS complex of wider than 0.12/0.14 seconds. Other indications of an abnormal heart rhythm are the repeatability of a signal as defined by the R-R interval between cardiac events. The greater the value is from zero, the more random the rhythm. A value of 20 ms over 10 samples would be an indication of VF.

A healthy QRS complex appears as a sharp spike and indicates that electrical waves are flowing through the heart properly. A rounded QRS complex is indicative of VT. Also a signal displaying low amplitude will lead to an automated external defibrillator (AED) recommending treatment.

Other factors of the ECG trace may also be used in determining whether the rhythm is shockable (e.g. P-wave presence and polarity, power spectrum density, time away from isoelectric baseline, FFT (Fast Fourier Transform)).

There are two potential periods where delays can occur in the operation of an automated external defibrillator. These are during the period where a capacitor in the defibrillator is being charged in order to deliver the shock to the patient, and also during the time where ECG rhythm recognition is being verified so that a decision to shock can be made. In known defibrillators the capacitor charge time can take between 8 and 9 seconds. This charging will occur without any indication of the patient's condition. Once charged, the analysis routines for the ECG generally take between 9 and 15 seconds. When these two periods are combined, it can be seen that the defibrillator can take anywhere up to 24 seconds from defibrillation pad application to treatment shock. Although regulations call for a detection, analysis and defibrillator charging time not exceeding a total of 30 seconds, a delay of even 24 seconds can greatly affect the survival rate of a patient.

External defibrillators often include, or operate in conjunction with, an electrocardiogram (ECG) rhythm recognition detector. The ECG has to differentiate abnormal heart rhythms, from all other cardiac rhythms. Other cardiac rhythms include normal sinus rhythms, supraventricular rhythms such as atrial fibrillation and atrial flutter, ventricular ectopy, idioventricular rhythms, asystole and organised cardiac rhythms such as those associated with the presence of pulse and blood pressure. Consequently, the signals that are analysed may contain a great deal of "noise", which can give inaccurate readings. If the impedance is not correctly measured, it may in fact not be in the range where it is safe to give a shock to the patient.

A known automated defibrillator is described in U.S. Pat. No. 6,029,085 in the name of SurVivaLink Corporation. In this document the defibrillator includes a monitoring and analysis circuit that analyses signals from electrodes attached to a patient's chest. An impedance between the electrodes is measured and if the impedance falls within a certain range, the apparatus will allow a shock to be delivered to the patient's heart. Charging of the defibrillator occurs automatically at the instant that the defibrillator is switched on and the charging process occurs as a separate process from the process involving subsequent analysis and treatment of the patient's condition by manually triggering of defibrillation.

A problem with known defibrillators is that there are no safety mechanisms, whereby charging of a defibrillator in readiness to deliver a shock to the patient's heart, only occurs in response to specific parameters measured for the heart. Further, when the patient's heart rhythm pattern is analysed, if further analysis is to be made, for example because of "noise" being measured in addition to the heart rhythms, the whole analysis process has to be restarted, so adding to delay in the treatment of a patient by shocking.

The present invention seeks to overcome problems associated with the prior art by providing an accurate and rapid analysis of the heart pattern, to provide charging of the device when only absolutely necessary and to reduce the time from application to shock delivery. In addition a further aim of the invention is to provide accurate readings of the heart rhythm to reduce the risk of applying a shock to a patient when not strictly needed.

According to a first aspect of the invention there is provided a defibrillator including;
 a) an analyser arranged to receive signals from a patient's heart,
 b) a charging circuit,
 c) electrodes arranged to deliver a charge from the charging circuit to the patient, wherein the analyser is arranged to compare one or more initial heart rhythm sequences from the patient with predetermined data relating to a heart rhythm and, depending on a result of an initial part of said comparison, the analyser is arranged to activate starting of charging of the charging circuit, whilst comparison continues, in readiness for possible delivery of a shock to the patient.

Preferably, the analyser is able, when the charging circuit is charged, to make a final data comparison analysis, to activate delivery of a shock to the patient via the electrodes, when merited.

The signal to the analyser is ideally split into segments. The segments may be analysed by the analyser, individually or as a whole. Preferably, four segments are analysed. The heart rhythm sequence or segments may be analysed on the basis of time duration and ideally a three-second duration for each segment is used. Alternatively the segments can be analysed on the basis of heart rate. It is possible that a combination of time duration and heart rate analysis can be used.

It is envisaged that the segments are compared with the pre-determined data and if a majority of the segments of the sequence are outside (or inside) parameters for the data, then shocking of the patient is allowed to occur.

It is desirable that the apparatus of the invention includes noise reduction circuitry or/and software to reduce extraneous signals.

It is advantageous that the analyser is arranged to compare the heart rhythm sequences with data held by a rhythm recognition system, which may be integral with other parts of the defibrillator.

A second aspect of the invention consists in a method of administering a shock to a patient by a) assessing the patient's cardiac rhythm;

b) comparing the rhythm with data and analysing the differences;

c) depending on the result of an initial part of the analysis, charging the defibrillator; and d) if the results of the whole analysis fall within certain parameters, delivering a shock to the patient.

Figure 2:
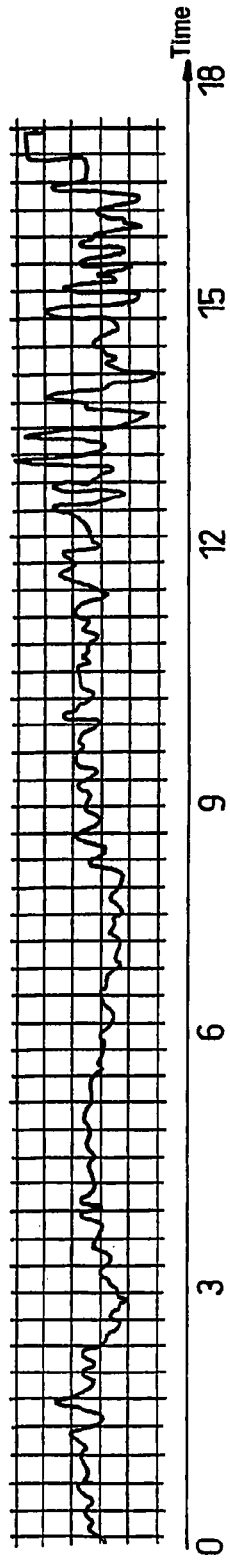

The invention can be performed in various ways and a specific embodiment will now be described by way of example, with reference to the accompanying drawings in which:

FIG. 1: Shows a schematic representation of a defibrillator according to the invention;

FIG. 2: Shows an ECG output of a heart rhythm; and

Figure 3:
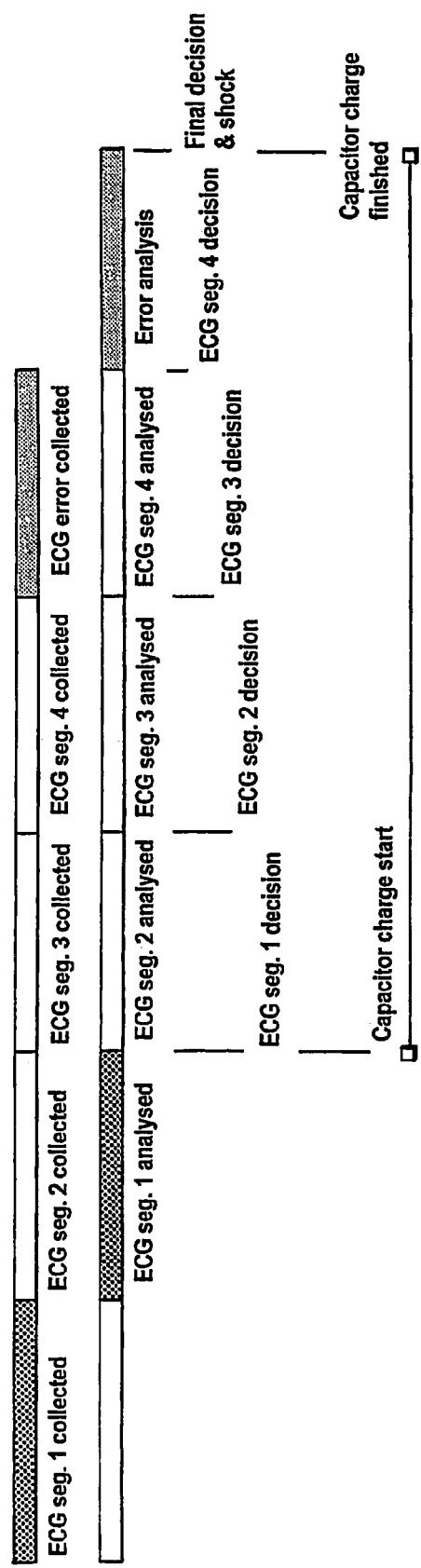

FIG. 3: Shows a time plan showing segment analysis and capacitor charging prior to shocking; and FIG. 4: shows a schematic outline of the shock procedure.

As shown in FIG. 1, the defibrillator 1 comprises an analyser 2, which receives signals that are detected from a patient's heart by electrodes 6. The electrodes comprise pads placed on the patient's chest. Information from the analyser is fed to a processor 3, which measures the signals received against data held by a rhythm recognition system. If the signals initially do not comply with parameters set by the data, then charging of the charging circuit 4 occurs. Charge is held by a capacitor 5. Charging occurs in readiness to give a shock to the patient. If, on the basis of further data analysed from the patient, the parameters set by the data held are not met, then the defibrillator sends a shock, or recommends a shock and then sends it after user confirmation, to the patient via electrodes 6, to regulate the patient's cardiac activity.

The processor 3 and analyser 2 can be a combined unit or they may be separate units. The processor could be a remote system, which collates information from, for example, a hospital data bank. Further it is envisaged that the rhythm recognition system could be in a remote location, such as a data bank in a hospital. Both the integral and the remote recognition systems can be updated with new information about heart rhythm patterns as new information is provided by research, or from individual patient records. It is also envisaged that the analyser may be arranged so that if the comparison with data parameters fall within certain limits, then charging is initiated, this in effect being a positive test for irregularities.

The defibrillation pads placed upon the patient's chest detect an ECG voltage signal. The analysis of the signal is then used in the decision of whether charging of the defibrillator is to occur. FIG. 2 shows an abnormal signal sequence produced by a heart beating over a period of 18 seconds). The signal passes through an ECG filter to reduce noise and is amplified. The signal is then passed onto a conventional analogue-to-digital converter (ADC), which produces a digital signal in response to the ECG voltages. The signal is then passed to a DATA/ADDRESS bus and then to a microprocessor and memory module. The signal is sampled by the microprocessor at desired frequency. It is desirable that the recognition of VT at 200 Microvolts or greater amplitude shall exceed 90% in the absence of 'noise'. Noise not only includes extraneous signals but also artefacts that distort signals. For detecting VT the sensitivity shall exceed 75%. The specificity of the detector in correctly identifying non-shockable rhythms should exceed 95% in the absence of noise. The data may be defined as an algorithm indicating ventricular fibrillation.

Two methods of sampling have been devised in order to acquire an accurate impression of the ECG waveform in the shortest possible time.

In a first analysing process as shown in FIG. 3, the ECG signal sequence is analysed for four, three-second, segments of the heart rhythm, the segments being of equal time duration. Although it is preferred that four segments of a three-second duration are analysed, the number of segments and the duration can be varied. The sampling frequency is preferably 100 to 200 HZ. 100 HZ is generally used during defibrillation, while 200 HZ allows a more in-depth analysis of the patient's condition following initial treatment. 100 HZ gives 300 samples per segment of heart sequence monitored, while 200 HZ gives 600 samples per segment.

A human heart acting normally will have a heart rate of 60-80 beats per minute. However a heart in ventricular fibrillation generally has a rate of between 180-300 beats per minute, while a heart in ventricular tachycardia generally will have a rate of over 180 beats per minute. Therefore, for a normal heart, a three-second segment will generally contain 3-5 QRS complexes (electrocardiograph expression of the electrical activation of the ventricular myocardium). For a heart in ventricular tachycardia, there may be 9 or more QRS complexes, while in ventricular fibrillation, the number of QRS complexes could be around 15. Therefore, it can be seen that as the heart condition becomes more abnormal and therefore more dangerous for the patient, then more complexes are measured. This has the benefit that more checks are made to ensure that the heart is truly acting abnormally and that there is not an error in the equipment, so minimising the risk of incorrect shocking of the patient. As can be seen from FIG. 3, if analysis of the first segment indicates a potential shockable condition, then capacitor charging commences (this condition though might only be indicated after analysis of 2 or more segments). This process allows for longer detection and analysis periods by effectively eliminating the separate charge time by using the analysis to control when charging occurs. Longer detection and analysis times can result in greater specificity and/or sensitivity by allowing the sampling of more ECG data.

In a second analysis process, the criteria for whether a patient's heart should be shocked or not is based on the actual heart rate. In this situation, each segment to be analysed is based on the number of QRS complexes, rather than the time period of segments analysed. Preferably, four segments are analysed, with each segment ideally being based on 9 QRS complexes. This method has the advantage that a fast analysis of the patient's condition can be provided. Fast analysis is paramount when the heart is in a critical condition. For example, when a heart rate of 300 beats per minute is occurring, a four-segment analysis would take place in 1.8 second segments, each segment containing 9 beats. Overall diagnosis time would be decreased to 7.2 seconds instead of 12 seconds, during a normal heart rate. Although the length of time of analysis is reduced, accuracy is not compromised because more beats are measured in the shorter time. If there is only a potential critical heart condition, an ECG would show a lower heart beat pattern than in the critical condition, for example 180 beats per minute or less. When using the number of heart beats as the measurement for segment sampling, having a slower heart rate will mean that the segments are sampled at a slower rate but this will allow for a more detailed analysis of the heart pattern to be performed. A more detailed analysis has advantages if the patient is not in a critical condition.

If a sensor in the defibrillator detects that the QRS complex analysis is predicted to be excessively long, because a heart rate is not raised to an excessive level, the second analysis method can be halted and the first analysis method used instead. This will ensure that analysis occurs in the minimum time possible.

If any one of the segments is outside normal limits of heart activity as indicated by the memory data, a charge controller sends a signal to start charging the charging circuit. If, when all the sequence segments are analysed, the majority of sequence segments are outside normal limits of heart activity indicated by the memory data, the discharging circuit is activated to deliver a shock to the patient. Alternatively, charging may be started by a system whereby, if the heart sequence segments fall within limits set by the memory data, then charging is initiated. The data could comprise information about rhythm patterns indicating heart failure.

Upon the result of "noise" the processor orders another segment to be sampled from the patient and discards the contaminated sample/segment. If the "noise" has a known cause e.g. patient being moved, or touched, or the presence of a mobile phone or power cable, the processor may prompt the user to make a correction e.g. "Patient and device must remain still"; "Do not make mobile phone calls near this unit", "Move patient away from all power devices" etc. As "noise" greatly increases analysis time and removes accuracy it is essential that it is reduced before entering this analysis stage. Due to the split segment analysis, only the previous segment of analysis has to be repeated.

A majority result of (3 or 4 out of 4) 'Shock' decisions is required for defibrillation to be recommended for a four-segment analysis. The majority percentages for other embodiments using varying number of segments will vary and may not be based on the percentages illustrated herein.

A result minority result of 'Shock' decisions (0 or 1 out of 4) will lead to the prompting of "No Shock Advised".

A result of a drawn number of 'Shock' decisions will lead the defibrillator to conduct another analysis segment and re-assess the patient's condition. Because the "voting" on what action is to be taken is now based on an odd number, a "draw" decision is impossible.

In a further embodiment, the defibrillator will add an additional segment to the analysis sequence per noise or draw a result and undertake its analysis decision upon the last four (or other segment amounts in differing embodiments) segments in the sequence.

Both of these embodiments speed up "time to shock" by avoiding complete reanalysis of the patient in the event of noise.

Figure 4:
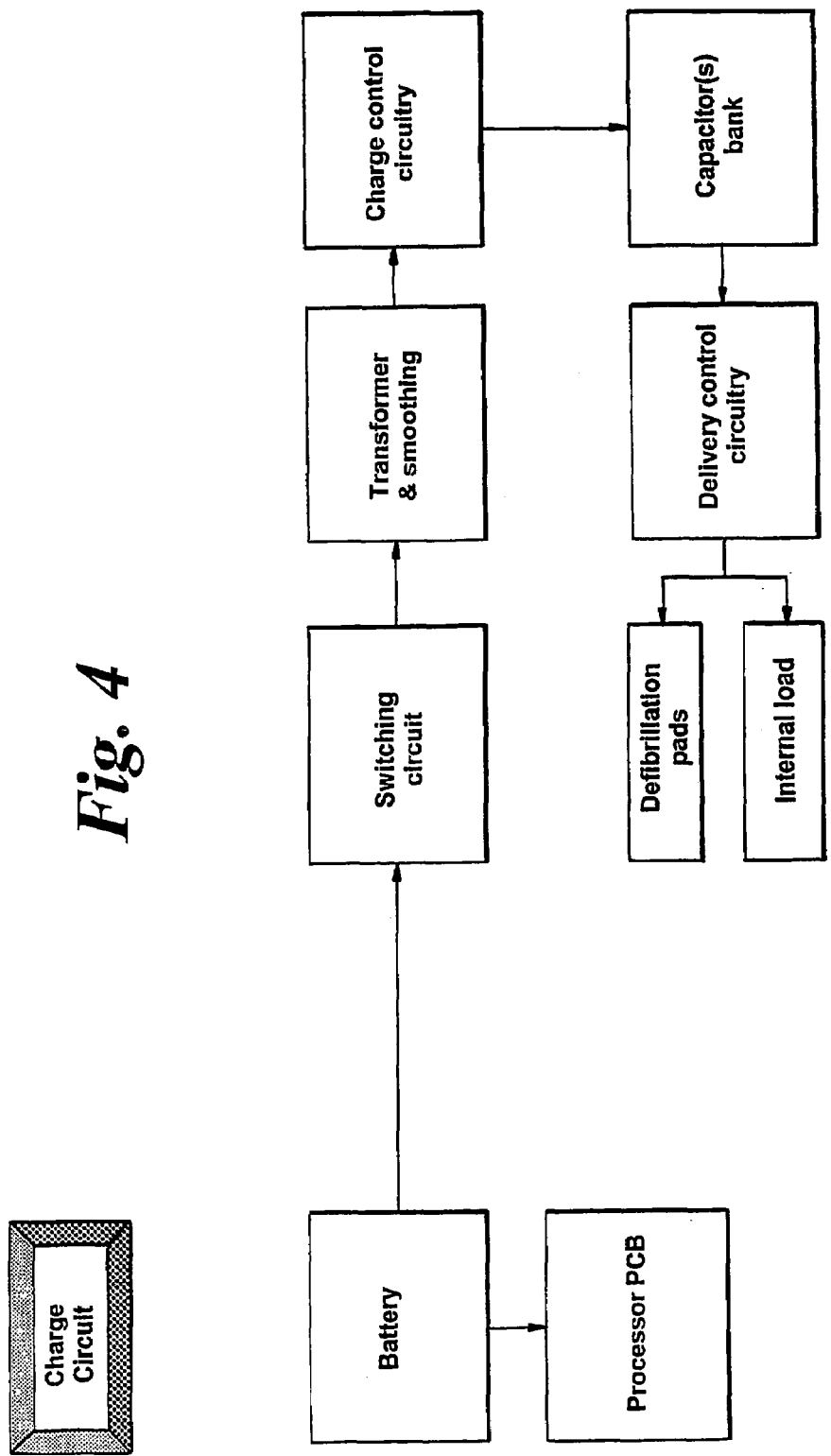

The shock circuitry and sequence operation is shown generally in FIG. 4.

Analysis of the initial segment indicates whether the ECG has detected a shockable condition for the patient and if so, then the processor initiates the charge sequence (as in FIG. 3). The charge sequence charges the capacitor(s) to a value determined by the patient's impedance, through a switch mechanism such as FET transistors.

Charging of the capacitor(s) occurs by allowing the input power circuit to flow therethrough, back to the ground line.

The charge on the capacitor is monitored during charging, by using a voltage comparator, which is placed in parallel (not shown).

Once the capacitor is charged to the predetermined level, the capacitor is isolated. The switching mechanism for outputting the defibrillation pulse to the patient is designed in such a way that should the mechanism fail, the discharge is directed to an internal load and does not present a voltage at the external pads on the patient.

In the first active charge mode the capacitors is continually refreshed so that the output is not effected by leakage current.

Once the processor acknowledges that a shock is desired it enters SHOCK mode. The processor prompts the user "Shock advised", to press a flashing button now to rescue and warns them to "stand clear".

The defibrillation pulse ideally should not be delivered during the first half of the T wave. During this time, known as the refractory period, the muscle is recovering from the contraction and returning to the resting state. Another shock at this time would be ineffective, as the cells would be unable to respond. The refractory period generally lasts 30 ms (milliseconds). However cells that are deprived of oxygen (ischaemic) can have a refractory period of up to 60 ms. The refractory period lasts for approximately 30% of an R-R interval.

Synchronised discharge is not a required feature of a defibrillator under current AAMI standard Nos DF2-4.3.17. However, to maximise the use of the defibrillator, it is of benefit if synchronised cardioversion is adopted. In cardioversion the peak of the defibrillator discharge ideally occurs within 60 ms of the peak of the R wave to obtain safe synchronised cardioversion. The discharge should occur on the negative gradient of the R-wave and should be synchronised thus. Failure to synchronise with the patient's QRS slope may precipitate ventricular fibrillation.

In order to discharge, the defibrillator uses a delivery control circuit. This may comprise SCRs where, for example, a first and second SCR is turned ON, while a third SCR and one or more IGBTs are turned OFF. This causes a positive discharge into the patient via the defibrillation pads.

At a predetermined time or voltage (software selectable) further IGBTs may be turned to OFF, while the IGBTs which are at the OFF position are turned ON. This results in the switching mechanism reversing the pulse. The time in switching between pulses must be less than 400+/−50 μsec.

Once the pulse voltage drops to a significant level or continues to a predetermined time (software selectable) then the switching mechanism turns to an OFF state, such that any potential pulse resulting from failure of the circuit is directed to an internal load.

Following discharge the capacitor is immediately charged again to a selected voltage level according to the patient impedance and the rescue stage. This allows the defibrillator to act more quickly on a second shock where a patient's survival rate would have dropped. Only at the end of the rescue, or during CPR, is the capacitor fully discharged to the internal load/load circuit.

The sample segments of the heart pattern are stored in the data memory and analysed by the microprocessor rhythm recognition system. This system detects and compares the ECG signal and decides whether the ECG sample in the segment is either "shockable" or "non-shockable". As a further embodiment, the degree of artefact could also be calculated and if above a threshold value would provide a "noise" decision.

If the result of a segment decision is "shockable", then the processor instructs the charge controller to begin charging the capacitor. Following the analysis of the first segment of ECG data, the next segment is passed into the rhythm recognition system from the data memory and another separate decision is taken as to whether to recommend a shock or not.

This process is continued until all the required ECG segments have passed through the rhythm recognition system. The ECG data sequence is then analysed and compared as a whole in a similar manner as above to identify spurious ECG behaviour.

The final treatment decision by the processor is based upon the number of "shock"/"non-shock"/"noise" sub-decisions made. A majority of individual "shock" decisions (or a minority or "non-shock"/"noise") would result in the processor recommending the user to press the defibrillator shock button to administer a treatment shock in semi-automatic mode or administering the shock itself in automatic mode.

The charge circuit may be chosen so that the charge time for the capacitor is such that no time delay occurs between the end of the rhythm recognition system and the administration of required treatment. In one embodiment this time is approximately twelve seconds, the time for four consecutive ECG "shock" votes.

Any other combination of sub-decisions results in a no-shock final result, or analysis of further segments. If the capacitor has been charged as a result of a spurious VF or VT episode in only a minority of the segments, then it is discharged to the internal load before any user interaction with the patient i.e. CPR. This improves the overall safety of the device.

If the final decision represents a high degree of "noise", then the AED may prompt the user to remove the source of the noise if it can be identified or/and prompt CPR and/or restart a further analysis depending on the stage of the rescue.

In a further embodiment it is also possible to use a continual averaging ECG analysis. The ECG signal is analysed in real time, with a vote being cast at ideally a second by second basis, for example, 12 seconds, 13 seconds, 14 seconds and so forth.

In the preferred embodiment the signal is continuously averaged with a last successive time period e.g. 3 seconds and a shock result before the mandatory 12-second analysis will result in a pre-emptive charging of the capacitor.

Hence, in this embodiment, each second of analysis would result in a vote decision being made on the previous three. Such averaging techniques would result in 10 consecutive votes. This is an enhancement on earlier 'segmented' analysis in that a higher accuracy can be obtained (for example, ten rather than four votes of three second duration).

Furthermore, non-sustained VF is easier to detect as the resolution of the voting system can now be regarded as one second as opposed to three or four seconds. A sporadic burst of VF lasting a second or less would be easily identifiable in that it would not appear in three consecutive analyses and could be discounted accordingly. Naturally, voting could be chosen to occur at any time length giving resolution higher or lower than this value. In complex cases, where VF present only in sporadic but life threatening bursts, a longer duration of window would result in a more reliable analysis.

In another embodiment, QRS complexes could be used instead of a definite time period. Hence in the preferred method, the collection of each three QRS complexes could result in a vote being cast. This further carries the advantage of VF being diagnosed and treated early while non-threatening rhythms such as PVC or NSR will be analysed in greater depth over a greater time period as described earlier.

In a separate embodiment, successive analysis could be keyed for cross-correlation (in effect singling out single QRS complexes) to further enhance the reliability of the method. This method would only function where QRS complexes had been identified and the exact sample time keyed to a number of known QRS lengths (obtained from the initial 3-second/x-QRS complexes analysis). By subtraction of each analysis waveform from the previous and integration (giving area-remaining) it is possible to ascertain whether the rhythm is VF (random; leaving a value) or VT/NSR (periodic; leaving no value). Naturally, sporadic rhythm changes (such as PVC's or non-sustained VF) would leave a value somewhere in-between.

It is to be understood that the above detailed description is an embodiment of the invention and is provided by way of example only. Various details of design and construction may be modified without departing from the true spirit and scope of the invention as described.

The invention claimed is:

1. A defibrillator, comprising:
   a) an analyzer arranged to receive signals from a patient's heart;
   b) a charging circuit; and
   c) electrodes arranged to deliver a charge from the charging circuit to the patient,
   wherein the analyzer is arranged to compare separately a plurality of segments of data each comprising a plurality of heart rhythm sequences from the patient with predetermined data relating to a heart rhythm and, depending on a result of the comparison of data of an initial one of the segments with said predetermined data, the analyzer activates charging of the charging circuit, whilst comparison of the remaining segments continues, in readiness for possible delivery of a shock to the patient, and the results of each of the separate comparisons of each of the remaining segments with the predetermined data are used to make a decision to enable the delivery of a shock.

2. The defibrillator according to claim 1, wherein the analyzer is adapted to make a decision to enable the delivery of a shock, based on accumulated decisions of the results of the separate comparisons of each segment of data.

3. The defibrillator according to claim 2, wherein the delivery of the shock is carried out either automatically, or by a user following an indication of the user, after the final decision is made.

4. The defibrillator according to claim 2, further comprising noise circuitry to reduce extraneous signals in the signal being analyzed.

5. The defibrillator according to claim 1, wherein the length of the segments is determined by one or more of time and the number of heart rhythm sequences.

6. The defibrillator according to claim 5, further comprising noise circuitry to reduce extraneous signals in the signal being analyzed.

7. The defibrillator according to claim 1, wherein the analyzer is adapted to analyze at least four segments of data and then make the decision to shock.

8. The defibrillator according to claim 7, further comprising noise circuitry to reduce extraneous signals in the signal being analyzed.

9. The defibrillator according to claim 1, wherein the analyzer is adapted to carry out a comparison analysis based on a time duration and/or heart rate.

10. The defibrillator according to claim 1, further comprising noise circuitry to reduce extraneous signals in the signal being analyzed.

11. The defibrillator according to claim 1, wherein said data is held in a rhythm recognition system, which is integral with the other parts of the defibrillator.

12. A method of administering a shock to a patient, comprising the steps of:
   a) assessing the patient's cardiac rhythm by producing a plurality of data segments containing data relating to the heart rhythm of a patient;
   b) comparing each of the segments with predetermined data and analyzing the differences;
   c) depending on the result of a comparison of an initial segment with the predetermined data, charging the defibrillator; and
   d) if the results of the comparison of each segment with the predetermined data fall within certain parameters, delivering a shock to the patient.

* * * * *